United States Patent [19]

Schammel et al.

[11] Patent Number: 4,755,622

[45] Date of Patent: Jul. 5, 1988

[54] PROCESS FOR THE PRODUCTION OF TRIMELLITIC ACID AND PYROMELLITIC ACID BY STAGED BROMINE ADDITION IN AN OXIDATION OF POLYALKYLAROMATICS

[75] Inventors: Wayne P. Schammel, Naperville; John K. Darin, deceased, late of Naperville, both of Ill., by Catherine L. Darin, administratrix

[73] Assignee: Amoco Corporation, Chicago, Ill.

[21] Appl. No.: 734,570

[22] Filed: May 15, 1985

Related U.S. Application Data

[63] Continuation-in-part of Ser. No. 566,585, Dec. 29, 1983, abandoned.

[51] Int. Cl.$^4$ ............................................. C07C 51/265
[52] U.S. Cl. ..................................... 562/413; 562/414; 562/416
[58] Field of Search ........................ 562/413, 416, 414

[56] References Cited

U.S. PATENT DOCUMENTS

| 3,686,293 | 8/1972 | Gualdi et al. | 562/413 |
| 3,920,735 | 11/1975 | Wampfler et al. | 562/416 |

FOREIGN PATENT DOCUMENTS

| 0704424 | 2/1965 | Canada | 562/413 |
| 1106751 | 10/1959 | Fed. Rep. of Germany | 562/413 |
| 0908736 | 10/1962 | United Kingdom | 562/413 |

Primary Examiner—Michael L. Shippen
Attorney, Agent, or Firm—James R. Henes; Gunar J. Blumberg; William H. Magidson

[57] ABSTRACT

This invention relates to the liquid-phase oxidation of pseudocumene and durene in the presence of multivalent catalyst promoted by a source of bromine and to conducting the oxidation in two steps so that the amount of bromine added in the first stage is about 10 to about 35 percent of the total bromine added and the remainder is added in the second stage.

18 Claims, No Drawings

PROCESS FOR THE PRODUCTION OF TRIMELLITIC ACID AND PYROMELLITIC ACID BY STAGED BROMINE ADDITION IN AN OXIDATION OF POLYALKYLAROMATICS

BACKGROUND OF THE INVENTION

This application is a continuation-in-part of application Ser. No. 566,585 filed Dec. 29, 1983, and now abandoned.

FIELD OF THE INVENTION

This invention relates to the liquid-phase oxidation of pseudocumene and durene in the presence of a multivalent catalyst promoted by a source of bromine and to conducting the oxidation in two steps so that the amount of bromine added in the first stage is about 10 to about 35 percent of the total bromine added and the remainder is added in the second stage.

The possibility of using liquid phase instead of vapor phase oxidation for the preparation of benzene carboxylic acids was first indicated by the disclosure in U.S. Pat. No. 2,245,528 of the catalysis provided by transition or variable valence metals, especially cobalt, in a liquid phase of saturated lower aliphatic acid at temperatures from 100° to 320° C. and pressures to maintain the liquid phase of the aliphatic acid. Such catalysis, according to said patent, was advantageously promoted by the use of a ketone, such as methylethyl ketone, or aldehyde, such as acetaldehyde. Unfortunately, such aldehyde or ketone promoted variable valence metal catalysis was useful only for converting mono-, di- or trimethylbenzenes to their respective benzene monocarboxylic acids: benzoic, toluic and dimethyl benzoic acids. Two separate, later, and somewhat parallel lower temperature (80°-100° C.) modifications of the aldehyde or ketone promoted cobalt catalysis in liquid phase of acetic acid did provide commercially feasible conversion of xylenes to phthalic acids, especially p-xylene to terephthalic acid, but only at the expense of using rather high concentrations of cobalt with respect to p-xylene.

The disadvantages of using high concentrations of cobalt promoted with large quantities of aldehyde or ketone were overcome and, at the same time, a greater choice of variable valence metal oxidation catalyst was made available and a wider choice of alkyl-substituted benzene starting materials for benzene di-, tri- and higher carboxylic acids was provided by the discovery of the unique promotional effect on said variable valence metal by bromine ion, provided per se or formed in situ with or without acidic reaction medium provided by $C_1$-$C_8$ monocarboxylic acids having no hydrogens on a tertiary carbon, such as benzoic acid and the saturated aliphatic monocarboxylic acids, preferably acetic acid. Such bromine-variable valent metal catalysis, first disclosed in U.S. Pat. No. 2,833,816, also provided, under liquid phase conditions over the temperature range of 120°-275° C., a substantially higher rate of oxidation (e.g. reaction duration of two hours or less for conversion of xylenes to high yields of phthalic acids) of alkyl side chains on the benzene ring to nuclear-substituted carboxylic acid groups and was not limited to such oxidative conversion of methyl side chains, but rather also applied to much longer side chains.

The bromine-polyvalent metal catalysts in acetic acid solvent have been in commercial use in many countries for the manufacture of terephthalic acid from p-xylene for many years. However, in the absence of acetic acid solvent, the best yield of a single phthalic acid (e.g., terephthalic acid) on a once-through basis of the xylene amounted to about 20 weight percent (12.8 mole %), according to U.S. Pat. No. 2,833,816.

According to U.S. Pat. No. 3,920,735 the Mn-Br and Co-Mn-Br catalyst systems are improved by the addition of zirconium. However, not mentioned, but illustrated in Tables I, II and IV in U.S. Pat. No. 3,920,735, is the fact that, when part of the zirconium is added, combustion of the feedstock to carbon dioxide increases.

In Canadian Pat. No. 704,424 Baldwin discloses a multistage oxidation system for preparing dicarboxylic acid. Improvements in commercial systems for obtaining maximum yields of aromatic carboxylic acids found in Baldwin's multistage oxidation system are the employment of a bromine-affording substance "in at least the final oxidation stage" and a technique for handling solvent and maintaining the solvent in the final oxidation zone under substantially anhydrous conditions. Baldwin discloses for his multistage oxidation system that a dimethylbenzene, in his example para-xylene, is oxidized by a continuous process wherein a bromine-affording substance is added to the first stage or, if not to the first stage, then "directly into the second stage." This Baldwin patent does not disclose or suggest a process of staged bromine addition in the oxidation of pseudocumene. Moreover, the Baldwin patent teaches away from a process of staged bromine addition since it specifically concentrates on a single point of bromine addition in a multistage oxidation system.

U.S. Pat. No. 3,920,735 of Wampfler et al. is directed to zirconium-enhanced activity of transition metal-bromine catalysis for oxidation of di- and trimethylbenzene in a liquid phase. The Wampfler et al. patent does not provide staged bromine addition or use any staged catalysis in pseudocumene oxidations.

U.S. Pat. No. 4,314,073 of Crooks relates to secondary oxidation in general, but does not disclose or suggest bromine staging.

SUMMARY OF THE INVENTION

Pseudocumene or durene is oxidized with molecular oxygen to trimellitic acid or pyromellitic acid, respectively, under liquid-phase conditions in the presence of a catalyst consisting of a source of cobalt, a source of manganese, plus a source of bromine which is calculated to provide a total bromine-to-metals atomic ratio of about 0.4 to about 10.0, at a temperature in the range of about 100° C. to about 250° C., which process comprises conducting the oxidation in two steps so that the amount of bromine added in the first stage is about 10 to about 35 percent of the total bromine added and the remainder is added in the second stage. The temperature in the last stage is upward from about 175° C. to about 250° C. and the temperature in the preceeding stage is between about 125° C. and about 165° C.

BRIEF DESCRIPTION OF THE INVENTION

Pseudocumene (PSC) or durene is oxidized with molecular oxygen to trimellitic acid (TMLA) or pyromellitic acid (PMLA), respectively, under liquid-phase conditions in the presence of a catalyst consisting of a source of cobalt, a source of manganese, plus a source of bromine which is calculated to provide a total bromine-to-metals atomic ratio of about 0.4 to about 10.0, at a temperature in the range of about 100° C. to about 250° C., which process comprises conducting the oxidation in two steps so that the amount of bromine added in the first stage is about 10 to about 35 percent of the total bromine added and the remainder is added in the second stage.

Thus, by charging initially only up to about 35 weight percent of the total bromine charged, our novel process provides fresh bromine to assist in completing the difficult PSC oxidation reaction. This staged bromine addition contributes to an increased yield of TMLA from PSC feedstock.

An advantage of our process is that significantly less high and low boiling impurities are formed. By adding most of the bromine at the end of the run when catalyst deactivation is most prevalent, higher yields of TMLA are obtained. Our novel process is particularly suitable for the oxidation of PSC to TMLA since the TMLA is, in many respects, a catalyst poison.

Our novel process relates to the liquid-phase oxidation of aromatic hydrocarbons having two or more alkyl groups attached to the aromatic ring, using cobalt, manganese and/or other variable-valence metals plus bromine with or without zirconium.

The source of molecular oxygen for the enhanced oxidation of this invention can vary in $O_2$ content from that of air to oxygen gas. Air is the preferred source of molecular oxygen for oxidations conducted at temperatures of 100° C. and above up to 250° C. The minimum pressure for such oxidations is that pressure which will maintain a substantial liquid phase of 70–80% of the reaction medium, either neat PSC, neat durene, or PSC or durene and 70–80% of the acetic acid. The acetic acid solvent, when used, can amount to 1–10 parts on a weight basis per part of the PSC or durene. The PSC or durene and/or acetic acid not in the liquid phase because of vaporization by heat of reaction is advantageously condensed and the condensate returned to the oxidation as a means for removing heat and thereby temperature controlling the exothermic oxidation reaction. Such vaporization of PSC or durene reactants and/or acetic acid solvent is also accompanied by vaporization of lower boiling by-product water. When it is desired to take advantage of the benefits of withdrawing acetic acid and water of reaction from the liquid-phase oxidation, as will be hereinafter demonstrated, condensate is not returned to the oxidation.

Our reaction, as applied to PSC or durene, is very difficult and has only been practiced as a batch process in the prior art for the oxidation of PSC or durene because the reaction products, TMLA or PMLA, are poisons for the catalyst. Batch reactions are successful because high concentrations of the product acid occur only near the end of the oxidation while in continuous oxidations the product concentration is at a constant high level. Batch oxidations, however, have disadvantages because the concentration of the hydrocarbon near the beginning of the oxidation is high and its rate of oxidation is difficult to control. This leads to a low concentration of dissolved oxygen and increased amounts of hydrocarbon radical reactions producing dimeric, high boiling side products which reduce the yield. Thermally- induced destruction of methyl groups of PSC or durene is also known to occur leading to xylenes which eventually become oxidized to dicarboxylic acid groups, thus leading to yield loss. In our novel process, we bypass the difficulties of both batch and continuous oxidations. In this two-step process, we first conduct a semi-continuous or batch oxidation in a manner so that (1) only about one to about two methyl groups on a benzene ring become oxidized to avoid catalyst poisoning, (2) the hydrocarbon concentration is kept low to eliminate much of the radical dimerization reactions, and (3) the temperature is maintained sufficiently low to minimize the destruction of methyl groups. Then, in the second step, we batch oxidize the resultant material from the semi-continuous or batch oxidation so that high concentrations of poisonous product acids occur only near the end of the oxidation.

The total bromine added can be from a single source of bromine, for example, ionic bromine sources (HBr, NaBr, $NH_4Br$ and the like) or from a combined form of bromine, for example, organic bromides such as benzyl bromide, tetrabromoethane and others.

Our invention also includes a process for the oxidation of PSC or durene with molecular oxygen to TMLA or PMLA under liquid-phase conditions in the presence of a manganese-bromine or cobalt-manganese-bromine catalyst, at a temperature in the range of about 100° C. to about 250° C. For oxidation of PSC or durene, the total concentration of catalyst metals, i.e., manganese or manganese plus cobalt, is in a range of about 2.0 to about 20 milligram atoms, and the concentration of bromine is in a range of about 1.5 to about 50 milligram atoms per gram mole of PSC or durene.

Our novel process relates to the liquid-phase oxidation of PSC or durene to TMLA or PMLA using cobalt, manganese and/or other variable-valence metals plus bromine and when desired, zirconium. A useful catalyst for our process is a zirconium-cobalt-manganese-bromine catalyst wherein the molecular ratio of zirconium to cobalt is about 1 to about 10 to about 1 to about 100 and the oxidation is conducted at a temperature in the range of about 100° C. to about 250° C., which process comprises conducting an oxidation of the pseudocumene or durene so that the first stage is a semi-continuous or alternatively is a batch-stage oxidation of PSC or durene. The staged bromine addition is conducted so that the concentration of bromine in the first stage is 0 to about 0.5 mole per mole of metals while all the remaining bromine is added during the second stage. The total amount of bromine added is about 50 to about 200 wt. % of the total metal catalysts present. The reaction is completed in a batch process at a temperature of about 140° C. to about 250° C. and, if desired, the solvent and water of reaction is withdrawn during the last 5 to about 20% of the period of the reaction, usually during the last 5 to 20 minutes of the reaction, thus leaving higher TMLA or PA concentrations in the liquid-phase oxidation reactor effluent.

Zirconium can be added to the reaction in any form soluble in the trimethylbenzene being oxidized or in acetic acid when it is being used as reaction solvent. For example, zirconium octanoate or naphthenate can be used with manganese and cobalt octanoates or naphthenates for oxidation of PSC or durene in the absence of reaction solvent and each of Zr, Mn, and Co can be conveniently used as its acetate when PSC or durene is oxidized in the presence of acetic acid solvent. Zirconium is available on a commercial basis as a solution of $ZrO_2$ in acetic acid and, as such, is ideally suited for liquid-phase oxidations using acetic acid as reaction solvent.

In a preferred embodiment, our process for the oxidation of pseudocumene or durene with molecular oxygen to trimellitic acid or pyromellitic acid, respectively, under liquid-phase conditions in the presence of a zirconium-cobalt-manganese-bromine catalyst wherein the atomic ratio of zirconium to cobalt is about 1:10 to about 1:100 at a temperature in the range of about 100° C. to about 250° C., comprises conducting a semi-continuous or batch oxidation of the pseudocumene or durene so that the amount of bromine in the first stage added is about 10 to about 35 percent of the total bromine added and the remainder is added in the second stage which is calculated to provide the total bromine-to-metals atomic ratio of about 0.4 to about 10.0, preferably in the range of about 0.5 to about 2.0 also keeping the concentration of pseudocumene or durene low so that only one methyl group on the average on the benzene ring is converted to a carboxylic acid group thus avoiding the poisoning of the catalyst and completing the reaction in a batch process at a temperature of about 100° C. to about 175° C. to about 150° C. to about 250° C.

For each gram mole of PSC or durene, the concentration of catalyst metals, i.e., zirconium and cobalt plus manganese, used is in a range of about 2.0 to about 20 milligram atoms total, and the concentration of bromine used is in a range of about 1.5 to about 50 milligram atoms total. Preferably, manganese is from 20% to about 100% of the total of manganese plus cobalt.

We have established a relationship between the structure of the carboxylic acid and its catalyst-poisoning ability, as shown in Table 1. The experiment described in Table 1 was designed so that the effect of adding specific types of aromatic acids on the rate of oxidation could be obtained. We define a decrease in the rate of oxidation upon addition of an acid as a poisoning effect. We find that at a water concentration of approximately 0.1%, TMLA, hemimellitic acid, and PA decrease the rate of oxidation by precipitating the catalyst metals from solution. Benzoic and phthalic acid do not have such an effect. Another type of poisoning effect is observed at a water concentration of 20% (see Part B of Table 1). Poisoning effects are now observed with phthalic, trimellitic, and hemimellitic acids but the poisoning is not caused by catalyst precipitation. Poisoning without catalyst precipitation occurs when there are two carboxylic acids ortho to each other on the aromatic ring. Catalyst precipitation may occur when there are two carboxylic acids ortho to each other on the aromatic ring but, additionally, one or more acid groups are present. Our novel process is applicable to the oxidation of PSC to TMLA and trimellitic anhydride (TMA) or durene to pyromellitic dianhydride (PMDA).

We show the poisoning effect of trimellitic acid and pyromellitic acid in Table 1. The information in Table 1 was obtained by oxidizing 10.0 ml of pseudocumene in 100 ml of acetic acid using a Co/Mn/Br catalyst (0.500 g and 0.492 g of the cobalt(II) and manganese(II) acetate tetrahydrates and 0.413 g of sodium bromide) at 95° C. and 1.0 atmosphere of air. The rate of oxidation is sufficiently slow so that the concentration of oxidized materials and hence the rate of oxidation remains essentially constant for 2–3 hours. During this time the water and aromatic acid concentration can be instantaneously changed by the appropriate addition into the reaction flask. Oxidation rates ranged from 0–7 ml O$_2$/min.

TABLE 1

THE EFFECT OF THE ADDITION OF SELECTED ACIDS TO A CO/MN/BR CATALYZED OXIDATION OF PSEUDOCUMENE

| ACID | ACID CONC., M | PERCENT CHANGE IN OXIDATION RATE | PERCENT CHANGE IN COBALT CONC. | PERCENT CHANGE IN MANGANESE CONC. |
|---|---|---|---|---|
| A. INITIAL CONC. OF WATER = 0.1%. | | | | |
| RUN NO. | | | | |
| 1  benzoic     | .95  | +2   | 0    | 0 |
| 2  o-phthalic  | .22  | +33  | 0    | 0 |
| 3  o-phthalic  | .57  | +25  | 0    | 0 |
| 4  trimellitic | .11  | +2   | −71  | −99 |
| 5  trimellitic | .30  | −33  | −84  | −100 |
| 6  trimellitic | .47  | −49  | −85  | −100 |
| 7  hemimellitic| .037 | −6   | −80  | −90 |
| 8  hemimellitic| .26  | −99  | −100 | −100 |
| 9  pyromellitic| .037 | −95  | −98  | −100 |
| 10 pyromellitic| .074 | −96  | −100 | −100 |
| B. INITIAL CONC. OF WATER = 20% | | | | |
| EXAMPLE | | | | |
| 11 benzoic     | .38  | 39   | 0    | 0 |
| 12 benzoic     | .76  | 9    | 0    | 0 |
| 13 o-phthalic  | .19  | −12  | 0    | 0 |
| 14 o-phthalic  | .76  | −97  | 0    | 0 |
| 15 isophthalic | .12  | 14   | 0    | 0 |
| 16 trimellitic | .19  | −8   | 0    | 0 |
| 17 trimellitic | .38  | −61  | 0    | 0 |
| 18 trimellitic | .57  | −96  | 0    | 0 |
| 19 hemimellitic| .038 | −77  | 0    | 0 |
| 20 hemimellitic| .076 | −96  | 0    | 0 |

In the batchwise oxidation of PSC or durene, the exothermic heat of reaction vaporizes some of the liquid solvent which is carried out of the reactor by the process air. The solvent is condensed and returned to the reactor as reflux. This liquid reflux is reheated toward the end of the reaction cycle to ensure temperatures high enough to bring the oxidation to completion. After reaction, the reactor contents are depressurized and PA or TMLA is crystallized out to form a 50–60% solids slurry (close to the maximum solids concentration that is pumpable). The solids are filtered out and further processed into final product. The filtrate is disposed of and, therefore, represents a significant yield loss.

A specific, improved oxidation process for the production of TMA or PMDA from PSC or durene feedstocks comprises the withdrawal of solvent and water of reaction during the last 5 to about 20% of the oxidation reaction time. Where our TMLA or PMLA recovery process includes a crystallization step, this allows us to increase the crystallizer effluent up to 70–75% solids instead of the 50–60% solids without our novel solvent draw-off process. The recovery of TMLA or PMLA by the filter increased from about 92.2% to about 97.0% and, where our TMLA or PA recovery process is by dehydration and fractionation of the total oxidation reactor effluent, our novel solvent draw-off process allows a savings of energy.

An alternate suitable embodiment of the present inventive oxidation of PSC or durene comprising the withdrawal of the condensed solvent, acetic acid and water of reaction during the last 5 to about 20% of the oxidation reaction period is conducted using acetic acid reaction medium in the weight ratio to PSC or durene of about 0.4:1.0 to about 4.0:1.0. The metal oxidation catalyst components are cobalt, zirconium and manganese or cobalt and manganese. The manganese component of the catalyst is at least 10 wt. %, preferably in the range of about 14.0 to about 60.0 wt. % based on the total weight of catalyst metals. The zirconium content of the total metals used is in the range of about 1.0 to about 5.0, preferably about 1.5 to about 4.0%, by weight of the total metals. The cobalt component of the catalyst is in the range of about 35 to about 90 wt. % of the total metals.

Another alternate and suitable mode of conduct for the catalytic liquid-phase air oxidation of PSC or durene to TMLA or PMLA is staged addition of the bromine component. This improved mode of conduct provides a shorter overall reaction cycle, reduces metals corrosion and contamination of desired crude product while improving the high yields of the desired acid and low production of methylphthalic acids' and formylphthalic acids' impurities which are features of the prior art.

It is particularly desirable to oxidize PSC or durene as completely as possible to TMLA or PMLA not only to obtain high yields of that acid product in the oxidation effluent but also to provide potential recovery of crude TMLA or PMLA products with low partial oxidation impurities without extensive oxidation of acetic acid. Low impurity formation is a goal also desirable because TMLA and PMLA are rather soluble in acetic acid and the methylphthalic acids' and formylphthalic acids' impurities appear to enhance the solubilities of TMLA and PMLA leading to contamination of the product precipitated from the oxidation effluent, especially a concentrate thereof. Thus, the partial oxidation products in the oxidation effluent have a limiting effect on TMLA and PMLA precipitations by crystallization from said effluent, making necessary additional processing steps to effect recovery of the remaining TMLA and PMLA solutes in the mother liquor after separation from first crop product crystals. Also, the presence of the impurities require special processing of the total crude TMLA and PMLA to obtain it in commercially acceptable quality as its intramolecular anhydride.

The present inventive staged addition of bromine for the catalytic liquid-phase air oxidation of PSC or durene to TMLA or PMLA is conducted using acetic acid reaction medium in the weight ratio to PSC or durene of about 0.5:1.0 to about 4.0:1.0. The metal oxidation catalyst components are cobalt, zirconium and manganese or cobalt and manganese. Total metal concentration based on a gram mole of PSC or durene is in the range of about 2.0 to about 20, preferably about 2.2 to about 15, milligram atoms in combination with a source of bromine providing a bromine concentration of about 1.5 to about 50.0, preferably about 1.6 to about 30.0, milligram atoms. The manganese component of the catalyst is at least 10 wt. %, preferably in the range of about 14.0 to about 60.0 wt. % based on the total weight of catalyst metals. The zirconium content of the total metals used is in the range of about 1.0 to about 5.0, preferably about 1.5 to about 4.0, percent by weight of total metals. The cobalt component of the catalyst is in the range of about 35 to about 90 wt. % of the total metals.

When the oxidation of PSC or durene is conducted batchwise, all of the PSC or durene and most (90-99%) of the acetic acid and initial amount of catalyst components are charged at or near oxidation initiation temperature, preferably at about 100° C. to about 165° C., and at a pressure to maintain liquid-phase conditions. Then, pressurized air is injected into the reaction mixture and the reaction temperature is permitted to increase by heat evolved by the oxidation reaction to about 175° C. to about 250° C.

In an advantageous embodiment of our process for the oxidation of PSC or durene, with molecular oxygen to TMA or PDA under liquid-phase conditions in the presence of a zirconium-cobalt-manganese-bromine catalyst, the atomic ratio of zirconium to cobalt is about 1:10 to about 1:100 and the initial temperature is in the range of about 100° C. to about 220° C. This process comprises conducting an oxidation of the PSC or durene so that in the first stage the amount of bromine added is below about 35 wt. % of the total bromine to be added. Also, this process comprises permitting only partial oxidation of the PSC or durene, thus avoiding the poisoning of the catalyst and completing the reaction in a batch process at a temperature of about 140° C. to about 175° C. to about 150° C. to about 250° C. During the last 5 to about 20 percent of the reaction time, the solvent and water of reaction are withdrawn leaving about 60 to about 75 wt. % solids in the crystallizer effluent.

In a suitable embodiment of our process for the oxidation of PSC or durene with molecular oxygen to TMLA or PA under liquid-phase conditions in the presence of a zirconium-cobalt-manganese-bromine catalyst, the molecular ratio of zirconium to cobalt is about 1:10 to about 1:100. This process comprises conducting a semi-continuous or batch oxidation of the PSC or durene so that in the first stage the amount of bromine added is below 20 weight percent of the total bromine to be added. The reaction is completed in a batch process at a temperature of about 100° C. to about 175° C. to about 150° C. to about 250° C.

In an alternate embodiment, our process for the oxidation of PSC or durene with molecular oxygen to TMLA or PA under liquid-phase conditions is conducted in the presence of a cobalt-manganese-bromine catalyst. This process comprises conducting a semi-continuous or batch oxidation of pseudocumene or durene so that in the first stage no bromine is added or not more than 35 percent of the total bromine is added. The reaction is completed in a batch process at a temperature of about 100° C. to about 175° C. to about 150° C. to about 250° C.

It has now been discovered that our novel staged bromine addition process can be further improved by running a semi-continuous oxidation at a partial conversion which is high enough so that the concentration of unreacted hydrocarbon is very low throughout the run, improving product quality and yields. The semi-continuous part of the oxidation is conducted so that the concentration of TMLA or durene is low, usually about 1-5 mole percent, thus preventing premature catalyst deactivation, and the bromine concentration is zero or below 35 percent of the total bromine added. The total bromine added is about 0.5 to about 1.5 moles per mole of cobalt. Thus, the theoretical oxygen uptake is somewhere between 1 and 2.5 moles $O_2$/mole hydrocarbon, with 1.5-2 moles being preferred. Because of side reactions, the actual oxygen uptake may be slightly higher. Also, the semicontinuous oxidation may be run at a low enough temperature, usually about 120° C. to about 200° C., to allow maintenance of an oxygen concentration above 0.5 percent in the vent gas, with 2-8 percent being preferred. After all the hydrocarbon has been pumped in, the oxidation is finished batchwise. In the batchwise step, the temperature of reaction is increased from about 140° C. to about 175° C. to about 150° C. to about 250° C. to compensate for the decreasing reaction rate. In this step, all, or at least 65%, of the bromine used in the catalysts is added.

A series of pilot plant runs were designed to determine the levels of intermediates and TMLA products during the course of semi-continuous oxidations of PSC. These experiments were performed by stopping the reaction at various times during semi-continuous oxidations of PSC. The run conditions were identical for all runs and the resulting components' data are listed in Table 3. In addition, the levels of the principal intermediates (dimethylbenzoic acids and methyl dibasic acids) and the % TMLA are plotted with reaction time.

Clearly, the species with one of the three methyl groups oxidized (dimethylbenzoic acids) are formed first, and their concentration is highest at 15–30 minutes. The monomethyl dicarboxylic acids are also formed early, but they peak at about 45 minutes into the run. The desired product, TMLA, does not appear in significant concentrations until about 45 minutes, but it then rises rapidly to its maximum at the conclusion of the run at 79 minutes.

In addition to these partial oxidation runs, we have performed runs to isolate the benefits in yield and product quality which are due to semi-continuous oxidation of PSC or durene. The results of these runs are in Table 4 and they indicate that significant yield and product quality benefits can be gained by operating in a semi-continuous mode rather than batch. Specifically, two comparisons were made, one using a commercial prevention air ramp which starts with a low air rate, reaches a plateau and then decreases, and the other using a high constant air rate to minimize oxygen starvation. In the air ramp comparison, the semi-continuous oxidation enjoys a 0.8 wt. % yield advantage, and the finished ester color is reduced by 65% compared to the batch. In the high constant air case, the yield difference is 2.4% and the color is again reduced substantially.

The following examples illustrate the preferred embodiment of this invention. It will be understood that the examples are for illustrative purposes only and do not purport to be wholly definitive with respect to the conditions and scope of the invention.

EXAMPLE 1

In this Example, data was obtained showing bromine staging in the oxidation of PSC to TMLA. Staging the bromine addition during PSC oxidations produces about a 2.3 mole percent yield improvement over current commercial operations. This yield advantage is due to reduction in high boiling point by-products of about 50 percent and a reduction in burning to carbon oxides of about 15 percent. This Example is for oxidation of PSC with 80 percent bromine staging.

PSC (225 g, 1.875 mole), glacial acetic acid (399 g, 6.53 mole), water (21 g, 1.17 mole), cobalt acetate (1.66 g, 0.0067 mole), manganese acetate (0.45 g, 0.0018 moles), zirconium (0.0136 g, 0.000149 moles) and hydrogen bromide (0.106 g, 0.0013 moles) were charged into a two liter titanium autoclave equipped with a stirrer, internal cooling coil, external electrical heater, and titanium knock-back condenser. After purging the autoclave with nitrogen and pressurizing to 150 psig, the initial charge was heated to a temperature of 320° F. Compressed air was sparged into the autoclave below the liquid level to start the oxidation. Throughout the oxidation a tail-out catalyst mixture containing additional hydrogen bromide was pumped into the autoclave.

The reaction temperature and pressure were increased during the oxidation to a maximum temperature of 410° F. and a maximum pressure of 400 psig. Oxygen and carbon dioxide in the vent gas from the autoclave were measured during oxidation. When the oxygen concentration in the vent gas reached 14.0 percent, the oxidation was terminated by stopping the flow of compressed air into the autoclave and maintaining total pressure with nitrogen. Additional hydrogen bromine used was 0.345 g (0.0043 mole) or 76.5 percent of the total hydrogen bromine (0.451 g). The tailout catalyst solution also added acetic acid (24.6 g, 0.410 mole), water (4.50 g, 0.250 mole), manganese acetate (0.087 g, 0.000356 mole), and zirconium (0.0010 g, 0.000109 mole), to the oxidation mixture.

After reaction, the total reactor effluent and wash were combined, mixed in a blender, and sampled. Samples of about 20 g each were evaporated gently on a steam bath for about 3 hours and then further dried in a vacuum oven at room temperature for 2 days. The dried solid residues were then analyzed by esterification gas chromatography for component analysis. Esterification gas chromatography technique quantifies the low and high boiling by-products.

The product analysis is given in Table 2.

TABLE 2

| EXAMPLE 1 - 80% Bromine Staging | | |
|---|---|---|
| | Wt. % of Solids | Mole % of Pseudocumene |
| Trimellitic acid | 93.0 | 90.5 |
| Intermediates | | |
| Dimethyl benzoic acids | 0.09 | 0.13 |
| Aldehydes | 0.22 | 0.30 |
| Methyl dibasic acids | 0.30 | 0.38 |
| Low Boilers | | |
| Phthalic acid | 0.60 | 0.74 |
| Terephthalic acid | 0.43 | 0.53 |
| Isophthalic acid | 0.51 | 0.63 |
| Other low boilers | 0.24 | 0.24 |
| High boiling impurities | 1.20 | 0.89 |
| Mole % $CO_2$ + CO | 5.1 | 5.7 |

COMPARATIVE EXAMPLE A

Comparative Example A was for an oxidation of PSC without bromine staging. PSC (225 g, 1.875 mole), glacial acetic acid (399 g, 6.53 mole), water (21 g, 1.17 mole), cobalt acetate (1.65, 0.0066 mole), manganese acetate (0.50 g, 0.0020 mole), zirconium (0.0090 g, 0.000099 mole), and hydrogen bromide (0.619 g, 0.00765 mole) were charged into a two liter titanium autoclave equipped with a stirrer, internal cooling coil, external electrical heater, and titanium knock-back condenser. After purging the autoclave with nitrogen and pressurizing to 150 psig, the initial charge was heated to a temperature of 320° F. Compressed air was sparged into the autoclave below the liquid level to start the oxidation. Throughout the oxidation a tail-out catalyst mixture containing only some additional zirconium and manganese was pumped into the autoclave.

The reaction temperature and pressure were increased during the oxidation to a maximum temperature of 410° F. and a main pressure of 400 psig. Oxygen and carbon dioxide in the vent gas from the autoclave were measured during oxidation. When the oxygen concentration in the vent gas reached 14.0 percent, the oxidation was terminated by stopping the flow of compressed air into the autoclave and maintaining total pressure with nitrogen. No additional hydrogen bromine was used. The tail-out catalyst solution added acetic acid (24.4 g, 0.406 mole), water (4.46 g, 0.248 mole), manganese acetate (0.104 g, 0.000425 mole), and zirconium (0.0123 g, 0.000134 mole) to the oxidation mixture.

TABLE 3

| Comparative Example A - Oxidation of Pseudocumene Without Bromine Staging | | |
|---|---|---|
| | Wt. % of Solids | Mole % of Pseudocumene |
| Trimellitic acid | 89.0 | 88.0 |
| Intermediates | | |
| Dimethyl benzoic acids | 0.12 | 0.17 |
| Aldehydes | 0.40 | 0.50 |
| Methyl dibasic acids | 0.27 | 0.34 |
| Low Boilers | | |
| Phthalic acid | 0.76 | 0.95 |
| Terephthalic acid | 0.42 | 0.53 |
| Isophthalic acid | 0.53 | 0.66 |
| Other low boilers | 0.31 | 0.31 |
| High Boilers | 2.38 | 1.80 |
| Mole % $CO_2$ + CO | 6.3 | 6.9 |

Staging the bromine addition during batch pseudocumene oxidations with hydrogen bromine produces a 2.5 mole percent yield advantage over this Comparative Example of batch oxidation.

COMPARATIVE EXAMPLE B AND EXAMPLES 2-4

The data in Table 4 represents average mole % yield breakdown for each type of oxidation. Comparative Example B or the base-case represents an average of 3 individual experiments while the different bromine staging oxidations are averages of two each. By averaging in this manner, one can represent more accurately the effects of bromine staging on the yield. The benefits of staging the bromine immediately become apparent when viewed in this manner.

TABLE 4

| Bromine Staging Oxidations of Pseudocumene | | | | |
|---|---|---|---|---|
| Example | B | 2 | 3 | 4 |
| Mole % Component | Base Case | 65% Bromine Staged | 80% Bromine Staged | 100% Bromine Staged |
| TMLA | 88.0 | 89.0 | 89.7 | 89.6 |
| Intermediates | 0.8 | 0.8 | 0.8 | 1.0 |
| Low Boilers | 2.5 | 2.5 | 2.5 | 2.5 |
| High Boilers | 1.8 | 1.2 | 1.0 | 0.9 |
| $CO_2$ | 6.9 | 6.5 | 6.0 | 6.0 |
| Run Time, min. | 67 | 66 | 67 | 66 |

COMPARATIVE EXAMPLE C AND EXAMPLES 5-8

In Table 5, we have assembled results from several bromine-staging runs and the amount of bromine which is staged ranges from 65 to 100%. In addition, we have included as Comparative Example C a base-case batch run with no bromine staging. Clearly, the wt. % of high boiling impurities decreases as one decreases the amount of bromine which is initially charged to the reactor. At the same time, one can see that the percent TMLA in the product increases.

These data indicate that substantial yield and product quality benefits are obtained by staging the bromine to the reactor. The optimum amount of bromine to be added initially is about 10–20% since this amount will ensure completion of reaction.

TABLE 5

| THE EFFECT OF BROMINE STAGING ON THE BATCH OXIDATION OF PSC | | | | | |
|---|---|---|---|---|---|
| Example | C | 5 | 6 | 7 | 8 |
| Run type | Batch Base Case[1] | Batch 65% Br Stage[2] | Batch 80% Br Stage[2] | Batch 90% Br Stage[2] | Batch 100% Br Stage[2] |
| Run time, min. | 74 | 70 | 73 | 75 | 70 |
| PSC burning, mole % $CO_x$ | 5.7 | 6.1 | 6.1 | 6.2 | 5.6 |
| Cake Analysis | | | | | |
| Wt. % OA | 0.80 | 0.77 | 0.76 | 0.65 | 0.71 |
| Wt. % IA + TA | 1.02 | 0.99 | 0.98 | 1.00 | 1.09 |
| Wt. % methyldibasic acids | 0.38 | 0.29 | 0.32 | 0.32 | 0.52 |
| Wt. % high boilers | 2.66 | 1.64 | 1.54 | 1.61 | 1.09 |
| Wt. % TMLA | 91.7 | 93.6 | 94.2 | — | 94.4 |
| Total cake accountability | 97.1 | 97.9 | 98.3 | — | 98.1 |

[1]Control - No bromine staging.
[2]Bromine staging means the percent of total bromine which is not added to the initial reaction mixture, e.g., 65% Br stage indicates that 35% of bromine was added initially and 65% was pumped gradually to the reactor throughout the run.

These reactions are carried out batchwise with an initiation temperature of about 100° C. to about 175° C. About 0–35% of the total bromine to be added is added to the initial reaction mixture. The remaining amount of bromine is added to the tail-out catalyst mixture also containing manganese and zirconium in acetic acid solvent. This tail-out mixture is added slowly to the reaction mixture as the reaction proceeds. Preferably, the tail-out mixture containing most of the bromine is added at a slow, steady rate from the initiation to the end of the run. The primary advantage of bromine staging is that yield and product quality benefits are obtained without having to resort to lower process temperatures or higher air rates.

COMPARATIVE EXAMPLE D AND EXAMPLE 9

In Table 6, we have assembled data showing the effect of bromine staging on TMLA yield and quality. All yields are based on PSC charged to batch oxidations. A batch oxidation reactor was charged with 100 parts by weight of PSC together with 180 parts of 90% acetic acid and an initial catalyst of 0.20 part cobalt, 0.05 part manganese, 0.005 part zirconium promoted with 0.275 part bromine using hydrogen bromide. The initial charge was heated to a temperature of about 160° C. and then air was introduced. After about 20 minutes of oxidation, a tail-out catalyst was added to the oxidizing mixture continuously over about 35 minutes. The total additional catalyst charged in the tail-out catalyst was 0.01 part manganese and 0.005 part zirconium. When the oxygen content of the vent gas coming from the oxidation mixture rapidly increased to above about 14%, the oxidation was terminated. The results of eight such runs were averaged and these averages are reported as Comparative Example D in Table 6.

Again, the batch oxidation reactor was charged with 100 parts by weight of PSC and 180 parts of 90% acetic acid. The initial charge of catalyst added to the reactor was 0.20 part cobalt, 0.05 part manganese, and 0.005 part zirconium, but promoted with only 0.055 part bromine.

Again, the initial charge was heated to a temperature of about 160° C. and then air was introduced. After about 3 minutes of oxidation, a tail-out catalyst was added to the oxidizing mixture continuously over about 52 minutes. The total additional catalyst charged in the tail-out catalyst was again 0.01 part manganese, 0.005 part zirconium and 0.34 part bromine using as a source of bromine tetrabromoethane. When the vent oxygen rapidly increased to over about 14%, the oxidation was terminated. The results of five such runs were averaged and these averages are reported as Example 9 in Table 6.

An average yield of TMLA obtained in eight reactions without using bromine staging is 87.4 mole % based on PSC in the hydrocarbon feed. An average yield of TMLA obtained in five reactions under comparable conditions with bromine staging is 89.5 mole %. The process using bromine staging obtains about a two and one-half percent higher yield than the same process without using bromine staging. Bromine staging reduced intermediate oxidation products by one-third.

TABLE 6

THE EFFECT OF BROMINE STAGING ON TMLA YIELD AND QUALITY

| Example | D NO BROMINE STAGING[2] | 9 BROMINE STAGING[3] |
|---|---|---|
| Yield[1], mole % | | |
| IA + TA | 3.3 | 3.0 |
| Methyldibasic acids | 0.6 | 0.4 |
| High Boilers | 2.0 | 1.4 |
| TMLA | 87.4 | 89.5 |
| $CO_x$ | 7.4 | 7.0 |

[1]Yields are based on PSC charged to batch oxidation.
[2]Yields are averages of eight oxidations.
[3]Yields are averages of five oxidations.

COMPARATIVE EXAMPLES E–H and EXAMPLES 10–13

One can also use bromine staging in a semi-continuous oxidation rather than batch to achieve additional benefits.

In Table 7 and Table 8 we have assembled results from several PSC oxidation runs to show the effect of bromine staging on a semi-continuous process for oxidation of PSC conducted at temperatures in two different ranges. Results for oxidations conducted at temperatures in the range of 160° C. to 210° C. are given in Table 7. A lower temperature of oxidation range of 120° C. to 175° C. was used to obtain results in Table 8.

TABLE 7

THE EFFECT OF BROMINE STAGING ON SEMI-CONTINUOUS OXIDATIONS OF PSC AT TEMPERATURES IN THE RANGE OF ABOUT 160° C. to 210° C.

| Example | E | 10 | F | 11 |
|---|---|---|---|---|
| Process | Batch | Batch | Semi-continous | Semi-continuous |
| With Bromine Staging | no | yes | no | yes |
| Yield, mole % | | | | |
| IA + TA | 2.5 | 2.5 | 2.3 | 2.9 |
| Methyl dibasic acids | 0.8 | 0.8 | 0.8 | 1.0 |
| High Boilers | 1.8 | 1.0 | 1.6 | 1.1 |
| TMLA | 88.0 | 89.7 | 87.4 | 88.4 |
| $CO_x$ | 6.9 | 6.0 | 7.9 | 6.6 |

TABLE 8

THE EFFECT OF BROMINE STAGING ON SEMI-CONTINUOUS OXIDATIONS OF PSC AT TEMPERATURES IN THE RANGE OF ABOUT 120° C. to 175° C.

| Example | G | 12 | H | 13 |
|---|---|---|---|---|
| Process | Batch | Batch | Semi-continous | Semi-continuous |
| With Bromine Staging | no | yes | no | yes |
| Yield, mole % | | | | |
| IA + TA | 1.9 | 1.9 | 1.4 | 2.1 |
| Methyl dibasic acids | 1.7 | 1.2 | 1.3 | 0.9 |
| High Boilers | 0.6 | 0.5 | 0.4 | 0.4 |
| TMLA | 91.5 | 92.5 | 92.8 | 93.0 |
| $CO_x$ | 4.4 | 3.9 | 4.0 | 3.7 |

EXAMPLES 14–16

Durene was oxidized in these examples of staged operation. 188 g of durene, 400 g of acetic acid, 21 g of water, 1.6 g cobalt(II) acetate tetrahydrate, 0.50 g of manganese(II) acetate tetrahydrate, 0.26 g of 48% aqueous hydrobromic acid, and 0.0090 g of zirconium (as the acetate oxide) were placed in a two-liter autoclave. The reactor was heated to 140° C. under a flow of nitrogen. The reaction was then initiated by passing a flow of air through the reactor at a rate of 0.78 cubic feet/min. The temperature was controlled by passing water through a coil which is contained within the reactor. At the time of initiation, a flow of additional solvent and catalyst was added to the reactor at a constant rate of 0.50 ml/min. This solution consisted of 1.16 g of manganese(II) acetate tetrahydrate, 60 g of water, 0.13 g of zirconium (as the acetate oxide), 11.44 g of 48% aqueous hydrobromic acid, and 328 g of acetic acid. The temperature and pressure were staged in the following manner:

| Time, min. | Pressure, psi | Temperature, °C. |
|---|---|---|
| 0 | 150 | 140 |
| 10 | 200 | 174 |
| 25 | 225 | 177 |
| 30 | 250 | 177 |
| 35 | 275 | 193 |
| 40 | 350 | 195 |
| 45 | 400 | 191 |
| 50 | 400 | 210 |
| 70 | 400 | 216 |

The results of this experiment and similar experiments in which the catalyst concentrations were doubled and then quadrupled are given in Table 9.

TABLE 9

THE EFFECT OF BROMINE STAGING ON THE BATCH OXIDATION OF DURENE[d]

| | Yield, mole % | | | | |
|---|---|---|---|---|---|
| Example Number | pyromellitic acid | trimellitic acid | phthalide[a] | methyl tri-acid[b] | carbon oxides[c] |
| 14 | 60.0 | 2.3 | 9.7 | 23 | 6.0 |
| 15 | 60.4 | 5.0 | 15 | 14.9 | 4.5 |
| 16 | 61.8 | .82 | 11.6 | 13.3 | 2.9 |

[a]1,2-dicarboxy-4,5-phthalide.
[b]1-methyl-2,4,5-tricarboxybenzene.
[c]75% of the observed carbon dioxide and carbon monoxide assumed to have come from the complete combustion of durene.
[d]The catalyst concentration in 111 is described in the example above. The catalyst concentration was exactly doubled in 112 and quadrupled in 113.

It is claimed:

1. A process for converting pseudocumene or durene to trimellitic acid or pyromellitic acid, respectively, which comprises catalytically oxidizing a pseudocumene or durene containing feedstock with a source of molecular oxygen under liquid-phase conditions in the presence of a catalyst comprising a source of cobalt, a source of manganese plus a source of bromine with or without a source of zirconium at a temperature in the range of about 100° C. to about 250° C., and in two stages, wherein the first stage is conducted batchwise or semi-continuously and the second stage is conducted batchwise, wherein addition of the bromine component is conducted so that about 10 to about 35 percent by weight of the total bromine is added in the first stage and the remainder is added in the second stage, wherein the temperature in the second stage is upward from about 175° C. to about 250° C. and the temperature in the first stage is between about 125° C. and about 165° C., wherein the two stage addition of the bromine component is conducted while the source of molecular oxygen is introduced to the feedstock.

2. The process of claim 1, wherein the catalyst comprises one or more heavy metal oxidation catalysts comprising zirconium, cobalt and manganese to provide about 2 to about 20 milligram atoms total metals per gram mole of pseudocumene or durene, and a source of bromine to provide a total of about 1.5 to about 50 milligram atoms total bromine per gram mole of pseudocumene or durene.

3. The process of claim 1, wherein the catalyst comprises one or more heavy metal oxidation catalysts comprising zirconium, cobalt, and manganese and wherein the zirconium content is about 1 to about 5 weight percent, the manganese content is about 14 to about 60 weight percent and the cobalt content is about 35 to about 90 weight percent, the amount of each metal present is given in weight percent of the total metals present and a source of bromine to provide a total amount of bromine added of about 50 to about 200 weight percent of the total metal catalyst present.

4. The process of claim 1, wherein the oxidation is in an acetic acid solvent in an oxidation zone wherein the weight ratio of acetic acid to pseudocumene or durene is in the range of about 0.5:1.0 to about 4.0:1.0, and the catalyst is a cobalt-manganese-bromine catalyst to provide about 2 to about 20 milligram atoms total metals per gram mole of pseudocumene or durene, and a source of bromine to provide a total of about 1.5 to about 50 milligram atoms total bromine per gram mole of pseudocumene or durene.

5. The process of claim 2, wherein the oxidation is in an acetic acid solvent in an oxidation zone wherein the weight ratio of acetic acid to pseudocumene or durene is in the range of about 0.5:1.0 to about 4.0:1.0, the catalyst is a zirconium-cobalt-manganese-bromine catalyst, and the atomic ratio of zirconium to cobalt is about 1:10 to about 1:100.

6. A process for converting pseudocumene or durene to trimellitic acid or pyromellitic acid, respectively, which comprises catalytically oxidizing a pseudocumene or durene containing feedstock with a source of molecular oxygen under liquid-phase conditions in the presence of a catalyst comprising a source of cobalt, a source of manganese plus a source of bromine with or without a source of zirconium at a temperature in the range of about 100° C. to about 250° C. in a two-step process wherein the first oxidation is a semi-continuous oxidation conducted at a temperature of about 100° C. to about 200° C. so that only about one to about two methyl groups on the average on each benzene ring are converted to carboxylic acid groups thus avoiding poisoning the catalyst and completing the oxidation of partially oxidized psuedocumene or durene to trimellitic acid or pyromellitic acid, respectively, in a batch oxidation process at a temperature of from about 140° C. to about 175° C. to about 150° C. to about 250° C. and conducting a staged addition of the bromine component so that about 10 to about 35 percent by weight of the total bromine is added in the first oxidation and the remainder is added in the second oxidation, and wherein the two-stage addition of bromine addition is conducted while the source of molecular oxygen is introduced to the feedstock.

7. The process of claim 6, wherein the catalyst comprises one or more heavy metal oxidation catalysts comprising zirconium, cobalt and manganese to provide about 2 to about 20 milligram atoms total metals per gram mole of pseudocumene or durene, and a source of bromine to provide a total of about 1.5 to about 50 milligram atoms total bromine per gram mole of pseudocumene or durene.

8. The process of claim 6, wherein the catalyst comprises one or more heavy metal oxidation catalysts comprising zirconium, cobalt, and manganese and wherein the zirconium content is about 1 to about 5 weight percent, the manganese content is about 14 to about 60 weight percent and the cobalt content is about 35 to about 90 weight percent, the amount of each metal present is given in weight percent of the total metals present and a source of bromine to provide a total amount of bromine added of about 50 to about 200 weight percent of the total metal catalyst present.

9. The process of claim 6, wherein the oxidation is in an acetic acid solvent in an oxidation zone wherein the weight ratio of acetic acid to pseudocumene or durene is in the range of about 0.5:1.0 to about 4.0:1.0, and the catalyst is a cobalt-manganese-bromine catalyst to provide about 2 to about 20 milligram atoms total metals per gram mole of pseudocumene or durene, and a source of bromine to provide a total of about 1.5 to about 50 milligram atoms total bromine per gram mole of pseudocumene or durene.

10. The process of claim 7, wherein the oxidation is in an acetic acid solvent in an oxidation zone wherein the weight ratio of acetic acid to pseudocumene or durene is in the range of about 0.5:1.0 to about 4.0:1.0, the catalyst is a zirconium-cobalt-manganese-bromine catalyst, and the atomic ratio of zirconium to cobalt is about 1:10 to about 1:100.

11. The process of claim 6, wherein the oxidation is conducted so that the heat of reaction is removed from the liquid phase by condensing to a liquid materials vaporized by the liquid-phase oxidation wherein the condensate is returned to the oxidation reaction during the first 80 to about 95 percent of the oxidation reaction and the condensate is withdrawn from the oxidation during the last 5 to about 20 percent of the oxidation reaction.

12. The process of claim 11, wherein the catalyst comprises one or more heavy metal oxidation catalysts comprising zirconium, cobalt and manganese to provide about 2 to about 20 milligram atoms total metals per gram mole of pseudocumene or durene, and a source of bromine to provide a total of about 1.5 to about 50 milligram atoms total bromine per gram mole of pseudocumene or durene.

13. The process of claim 11, wherein the catalyst comprises one or more heavy metal oxidation catalysts comprising zirconium, cobalt, and manganese and wherein the zirconium content is about 1 to about 5 weight percent, the manganese content is about 14 to about 60 weight percent and the cobalt content is about 35 to about 90 weight percent, the amount of each metal present is given in weight percent of the total metals present, and a source of bromine to provide a total amount of bromine added of about 50 to about 200 weight percent of the total metal catalyst present.

14. The process of claim 11, wherein the oxidation is in an acetic acid solvent in an oxidation zone wherein the weight ratio of acetic acid to pseudocumene or durene is in the range of about 0.5:1.0 to about 4.0:1.0, and the catalyst is a cobalt-manganese-bromine catalyst to provide about 2 to about 20 milligram atoms total metals per gram mole of pseudocumene or durene, and a source of bromine to provide a total of about 1.5 to about 50 milligram atoms total bromine per gram mole of pseudocumene or durene.

15. The process of claim 12, wherein the oxidation is in an acetic acid solvent in an oxidation zone wherein the weight ratio of acetic acid to pseudocumene or durene is in the range of about 0.5:1.0 to about 2.5:1.0, the catalyst is a zirconium-cobalt-manganese-bromine catalyst, and the atomic ratio of zirconium to cobalt is about 1:10 to about 1:100.

16. The process of claim 1, wherein the oxidation is a two-step process in an acetic acid solvent and the catalyst comprises one or more heavy metal oxidation catalysts comprising zirconium, cobalt and manganese to provide about 2 to about 20 milligram atoms total metals per gram mole of pseudocumene or durene and a source of bromine, and wherein the first oxidation is a semi-continuous oxidation conducted at a temperature of about 100° C. to about 200° C. so that only about one to about two methyl groups on the average on each benzene ring are converted to carboxylic acid groups thus avoiding poisoning the catalyst and completing the oxidation of partially oxidized pseudocumene or durene to trimellitic acid or pyromellitic acid, respectively, in a batch process at a temperature of from about 140° C. to about 250° C.

17. The process of claim 1, wherein the oxidation is in an acetic acid solvent, the weight ratio of acetic acid to pseudocumene or durene is in the range of about 0.5:1.0 to about 4.0:1.0, the catalyst is a zirconium-cobalt-manganese-bromine catalyst, and the atomic ratio of zirconium to cobalt is about 1:10 to about 1:100.

18. The process of claim 16, wherein the weight ratio of acetic acid to pseudocumene or durene is in the range of about 0.5:1.0 to about 4.0:1.0, the catalyst is a zirconium-cobalt-manganese-bromine catalyst, and the atomic ratio of zirconium to cobalt is about 1:10 to about 1:100.

* * * * *

UNITED STATES PATENT OFFICE
CERTIFICATE OF CORRECTION

Patent No. 4,755,622         Dated  July 5, 1988

Inventor(s)  W.P. Schammel & J. K. Darin by Catherine L. Darin

It is certified that error appears in the above-identified patent and that said Letters Patent are hereby corrected as shown below:

Column 8, line 6, "PDA" should be --PMDA--.

Signed and Sealed this

Twenty-ninth Day of November, 1988

*Attest:*

DONALD J. QUIGG

*Attesting Officer*     *Commissioner of Patents and Trademarks*